United States Patent [19]
Kastenbauer et al.

[11] Patent Number: 5,897,491
[45] Date of Patent: Apr. 27, 1999

[54] DEVICE FOR ENDOSCOPIC EXAMINATIONS

[75] Inventors: Ernst Kastenbauer, Berg; Jens Feyh, Munich, both of Germany

[73] Assignee: Explorent Chirurgische Instruments GmbH, Tuttlingen, Germany

[21] Appl. No.: 08/836,681

[22] PCT Filed: Aug. 16, 1996

[86] PCT No.: PCT/EP96/03613

§ 371 Date: Jun. 27, 1997

§ 102(e) Date: Jun. 27, 1997

[87] PCT Pub. No.: WO97/07732

PCT Pub. Date: Mar. 6, 1997

[30] Foreign Application Priority Data

Aug. 30, 1995 [DE] Germany ............... 195 32 098

[51] Int. Cl.⁶ .................................................. A61B 11/02
[52] U.S. Cl. .................... 600/239; 600/237; 600/238; 600/242
[58] Field of Search .................... 600/102, 160, 600/227, 228, 231, 232, 235, 237, 230, 239, 240, 241, 242, 243, 244, 245, 101, 175, 177, 178

[56] References Cited

U.S. PATENT DOCUMENTS

| | | | |
|---|---|---|---|
| 1,764,167 | 6/1930 | Highberg et al. | 600/239 |
| 2,969,059 | 1/1961 | Meek et al. | 600/239 |
| 3,241,550 | 3/1966 | Gelarie | 600/242 |
| 3,320,948 | 5/1967 | Martin | 128/17 |
| 4,151,837 | 5/1979 | Millard et al. | 128/12 |
| 4,300,541 | 11/1981 | Burgin | 128/18 |
| 5,063,908 | 11/1991 | Collins | 128/17 |
| 5,178,132 | 1/1993 | Mahefky | 600/241 X |

FOREIGN PATENT DOCUMENTS

2189148  10/1987  United Kingdom.

*Primary Examiner*—Beverly M. Flanagan
*Attorney, Agent, or Firm*—Pandiscio & Pandiscio

[57] ABSTRACT

A device for endoscopic examinations and operations includes a frame on which one or more of holding, connecting and receiving elements for locking and/or spreading instruments, lighting devices, liquid and/or gas suction devices, examination and/or surgical instruments may be arranged and detachably secured, as may also tongue and labial commissure retaining spatulas, palatal plates, lighting and receiving members for other devices and/or instruments.

30 Claims, 4 Drawing Sheets

DEVICE FOR ENDOSCOPIC EXAMINATIONS

BACKGROUND OF THE INVENTION

1. Field of the Invention

The invention is directed towards a device for endoscopic examinations and/or operations, in particular in the region of the epipharynx, oropharynx, mesopharynx and/or hypopharynx and/or of the larynx, but also, in optionally modified form, for cardiosurgical, laparoscopic, neurosurgical and/or gynaecological examinations and/or operations.

2. Description of the Prior Art

In the aforementioned region of the pharynx and of the larynx a large number of pathological changes may occur which not uncommonly require surgical therapy. For instance, besides benign tumors, carcinomas occur of the pharynx, for example pharyngeal lymphoepithelioma, and of the larynx, for example in the form of carcinoma of the sphenocephalus. Depending on the site of these tumors, a pharyngectomy or a laryngectomy is carried out in these cases. With a view to diagnosis of tumors in the region of the pharynx, use is made of a so-called laryngoscope, an endoscope with a spatula for pressing the tongue against the floor of the mouth and also optionally a laryngeal spatula. With the aid of such a laryngoscope it is also possible to operate by means of laser surgery, but both diagnosis and therapy prove difficult in many cases, for example when a tumor is located in the valleculae; this difficulty results from the tube diameter of such a laryngoscope. In the region of the transition from the oropharynx or mesopharynx to the hypopharynx, malignant tumors are to be found with increased incidence, the removal of which by laser surgery has hitherto been made decidedly difficult as a consequence of the intermittent use during surgery of instruments for representing the corresponding anatomical region. Moreover, there are a number of other problems, particularly in the region of the oropharynx and mesopharynx, which necessitate surgical intervention, for example tonsillectomy. In all these cases it is possible in principle for diagnosis and/or surgical intervention to be undertaken through the pharynx; however, on account of the convoluted structure thereof and the limited capacity of a patient to open his mouth wide it is extremely difficult to insert appropriate examining and/or surgical instruments as far as the location in question.

Similar difficulties also arise within the scope of endoscopy-based diagnostic measures and/or of surgical therapies in the region of other organs of the body, for example in the case of cardiosurgery, laparoscopy, neurosurgery or gynaecology. Here too, the access path is often very cramped, so that examinations and/or operations are greatly impeded.

This disadvantage of the known state of the art results in the problem that gives rise to the invention, namely of creating a device with which endoscopic examinations and/or operations, in particular in the region of the pharynx and of the larynx, can be performed without this entailing the need for a largely rigid instrument with a large tube cross-section, as is the case with conventional endoscopes, to be pushed forward as far as the location in question and without an operation having in certain circumstances to be carried out without direct view. Furthermore, there is a need for enlargement of the access path and for dynamic regulation of all anatomical areas of the region in question in order that the operation may become more precise and thereby safer.

SUMMARY OF THE INVENTION

The solution to this problem is achieved in the case of a generic device by virtue of a design according to the invention as described in the main claim. The core of the device according to the invention is formed by a rigid framework which, for example, can be fixed with a chest support and which serves to attach a plurality of instruments, in particular locking and spreading instruments for holding the mouth open, such as lingual and labial-commissure spatulas and also, in certain circumstances, a palatal plate, for auxiliary instruments such as lighting and suction devices, for examining instruments such as laryngoscopes and also for surgical instruments such as forceps and scalpels for tonsillectomy or for instruments for laser surgery. By means of the palatal plate according to the invention the mouth of a patient can be pushed wide apart, a lingual spatula presses the tongue largely out of the field of view and can, in certain circumstances, be combined with a laryngeal spatula which induces raising of the epiglottis and thereby opens the larynx. Labial-commissure spatulas spread the buccae apart laterally in order to create an access for aids and instruments that is as wide as possible. By way of aids, use may be made in particular of lighting means, suction devices or the like which create optimal conditions for a diagnosis or an operation. Finally, the examining and/or surgical instruments can be moveably secured to the framework according to the invention, in order on the one hand to stabilise their position and on the other hand to make exact movements possible. By this means the precision of an intervention can be increased, so that the burden on a patient is reduced.

For holding a plurality of aids and/or instruments use is made of one or more elongated, stable frame-elements, on which the means and/or instruments in question can be clamped or displaced. In a preferred embodiment two such attachment frame-elements are present which are approximately parallel to one another, which exhibit a spacing of about 5 to 10 cm and which, during use, extend approximately parallel to the buccae of a patient. These frame-elements serve, inter alia, to clamp firmly one labial-commissure spatula each; in order in this connection to be able to accommodate in positive manner the forces arising in the course of a spreading-out movement, the attachment frame-elements, on which the approximately sleeve-shaped holding parts for a labial-commissure spatula are pushed in positive manner, are provided with a polygonal cross-section, in particular a square cross-section.

These two attachment frame-elements are connected to one another by means of a crosspiece, located approximately in the region of the mentum of a patient, so as to form a preferably U-shaped, optionally also rounded or rectangular, attachment framework and/or attachment frame. In order to be able to adapt this framework to the oral width and the mandibular width of a patient, the attachment frame-elements may be designed to be adjustable in relation to the crosspiece about axes of rotation which extend perpendicular to the base surface of the U-shaped attachment framework. This possibility of adjustment can, for example, be brought about by means of a screw-clamp mechanism having a clamp screw that functions at the same time as a swivel joint.

The crosspiece of the U-shaped attachment framework additionally bears a receiving means for a lingual spatula and also a connecting element for a chest support. This receiving means for the lingual spatula is arranged in such a way that the longitudinal axis of the lingual spatula extends approximately perpendicular to the base plane of the U-shaped attachment framework, so that the attachment frame-elements extend close to the buccae of a patient.

In a first embodiment, which resembles the basic form of a conventional laryngoscope, the receptacle for a lingual spatula is arranged rigidly on the crosspiece. In this case the mouth can be opened by tilting back the head of a patient lying on his dorsum, so that a palatal plate is not absolutely essential. In practice, however, an arrangement has proved useful in which the receiving means for the lingual spatula is displaceable in relation to the crosspiece along an axis which is approximately parallel to the attachment frame-elements. This arrangement is suitable in particular for a further development of the invention, wherein on the free ends of the attachment frame-elements located opposite the crosspiece a transverse frame-element is arranged having a plate which is applied to the palate of a patient and thereby defines the position of the U-shaped attachment framework. If the receiving means for the lingual spatula is now displaced in relation to the crosspiece, then the mandible of a patient opens in the process, resulting in a functionally reliable mouth gag. In order to make such adjustability possible, the receiving means for the lingual spatula is arranged at the upper end of a column which passes through a guide element of the crosspiece and may simultaneously be provided at its lower end with a connecting element for a chest support. With the aid of transmission mechanisms, both adjustment and locking of the column that bears the lingual spatula can be brought about.

A possibility of adjustment may be provided, in order to be able to adapt the effective length of the lingual spatula projecting into the pharynx to a patient. To this-end the handle part of the lingual spatula may be received in a guide profile, it being possible for the displacement position of the spatula to be preset with an adjusting screw.

The invention makes use of lingual spatulas that have been expressly designed for this attachment framework; said spatulas are distinguished by an approximately spoon-type tongue part and, adjacent thereto, a straight holding part which is not inclined or only slightly inclined in relation to the tongue part, the entire lingual spatula being produced from a rigid and solid material, for example a sheet of stainless steel 2.5 mm thick, in particular being stamped out and bent. For the purpose of longitudinal adjustment the holding part is constructed with a constant cross-section and comprises on its underside a row of teeth formed by milled notches extending transversely, with which an adjusting toothed wheel of the receiving means described above can engage. The lower part of the spoon-type tongue part may be provided with a friction-augmenting profile. Furthermore, different shapes of the spoon-type tongue part are possible: in a standard design the latter is almost completely plane and inclined by only a few degrees in relation to the rear holding part. In a second embodiment the tongue part may be curved towards the underside in the manner of an arch, similarly to the laryngeal spatula of a conventional laryngoscope, so that the free end of the tongue part forms with the holding part an angle of about 15 to 25°. Furthermore it is possible, departing from the spoon shape, to provide a lateral cut-out on one or both sides of the tongue part in order to permit examinations and/or operations in the regions exposed by it. In addition it is possible to impress a curvature on the tongue part in the transverse direction in such a way that the lateral regions of the tongue part recede upwards and injuries to the tongue are avoided.

The palatal plate already referred to above for the support of the palate of a patient is provided, according to the invention, with a frame-element having bushings arranged at its ends, each of which can be pushed onto a free end of the U-shaped attachment framework as far as a stop element arranged there. For the purpose of receiving the dentes incisivi and/or the alveolar crest of the maxilla the palatal plate may be curved continuously downwards in its longitudinal direction in concave manner or in the form of a saddle.

The labial-commissure spatulas provided by the inventors for lateral spreading of the buccae have an elongated, narrow basic form. With a view to avoiding injuries to the patient, the front edge of such labial-commissure spatulas is rounded and such a spatula consists moreover of a material of limited elasticity, for example a soft metallic sheet having a thickness of 1.5 to 2 mm. For the purpose of setting the spreading angle of such labial-commissure spatulas, use is made of the attachment element thereof, which for this purpose is provided with an articulation means and/or adjusting means. Such labial-commissure spatulas may also be used for spreading the lateral wall of the hypopharynx. A labial-commissure spatula is inserted in this region by being pushed further forward in its guide in the direction of the hypopharynx and provides valuable assistance there to the extent that the sinus piriformis, in which about 90% of all carcinomas of the hypopharynx originate, is held open during the operation.

According to the invention a lighting means is further provided which may be formed from a system of lenses with a rear screw connection for a fibre-optic cable and which is connected by means of a ball-and-socket joint arranged on the casing of this element to a clip with a view to firm clamping to one of the two attachment frame-elements. A similar clip may comprise, instead of the lighting-means and/or ball-and-socket joint, a second attachment clip in which, for example, a suction tube or an instrument can be inserted and firmly clamped.

BRIEF DESCRIPTION OF THE DRAWINGS

Further particulars, features and advantages on the basis of the invention result from the following description of a preferred embodiment example of the invention and also by reference to the drawing. The latter shows in.

DETAILED DESCRIPTION OF THE INVENTION

Figure 1:
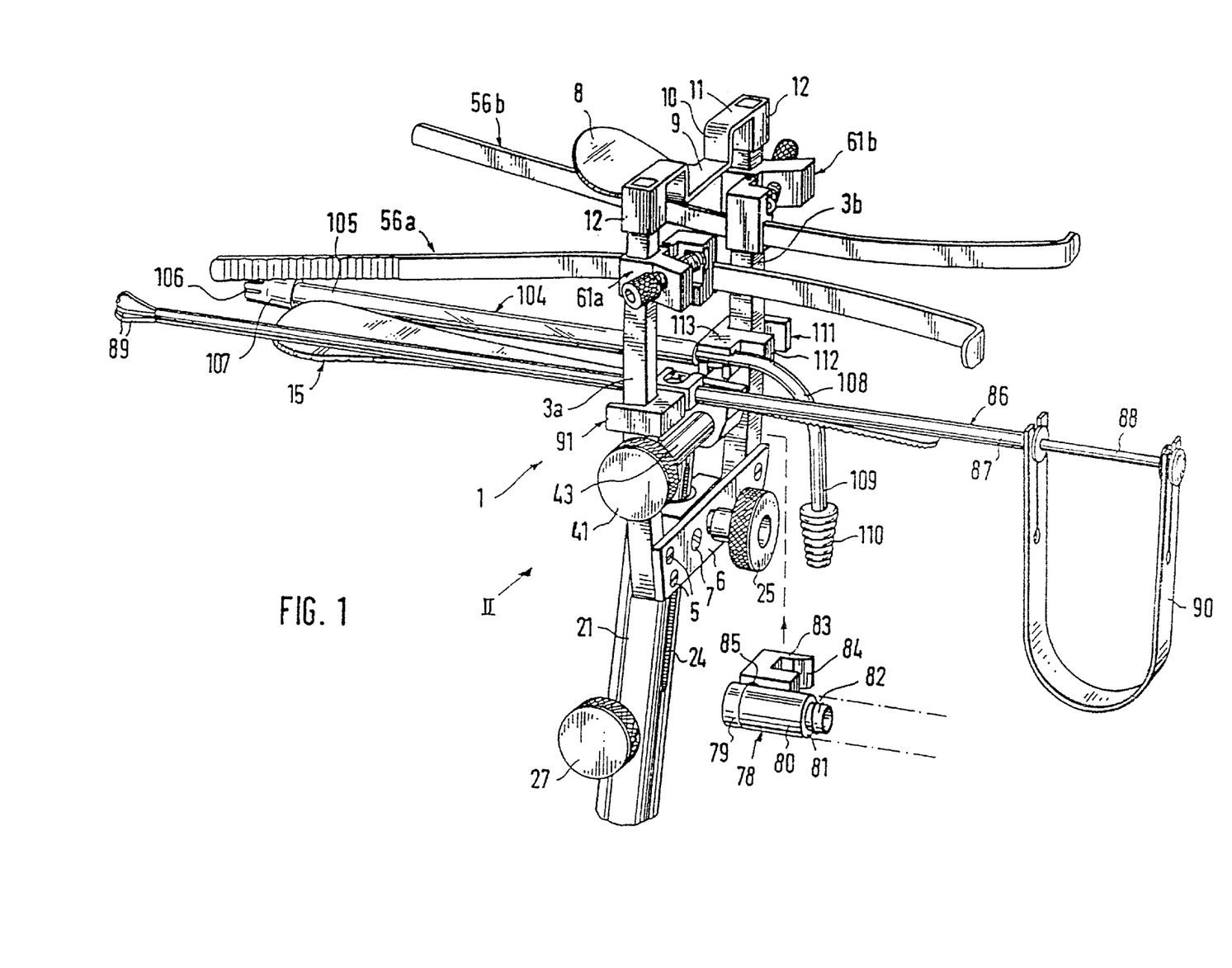
FIG. 1 an axonometric view of a device according to the invention, partly disassembled.

In FIG. 1 a supporting epi-oro-hypopharyngo-laryngoscope 1 is represented with a plurality of appended aids and instruments. With a view to promoting comprehension at a glance, reference will therefore firstly be made to FIG. 2, in which the majority of the appended parts have been omitted so that the actual framework 2 of the pharyngo-laryngoscope 1 according to the invention can be discerned more clearly. The framework 2 comprises two frame-elements 3a, 3b which have a constant, approximately square cross-section. These two frame-elements 3a, 3b are slightly curved with a radius of curvature of about 25 to 40 cm and are connected at their lower ends 4 by means of a screwed-on 5 transverse frame-element 6 so as to form a plane, approximately U-shaped framework 2. The attachment screws 5 in question are arranged on the transverse frame-element 6 in such a way that the free upper ends 7 of the two frame-elements 3a, 3b extend approximately parallel to one another, whereas the lower ends 4 converge towards one another by reason of the curved shape. This inherently rigid framework 2 of the pharyngo-laryngoscope 1 according to the invention serves to fix a plurality of locking, spreading and auxiliary means, examining instruments and surgical instruments as well as a connecting element for a chest support.

Figure 2:
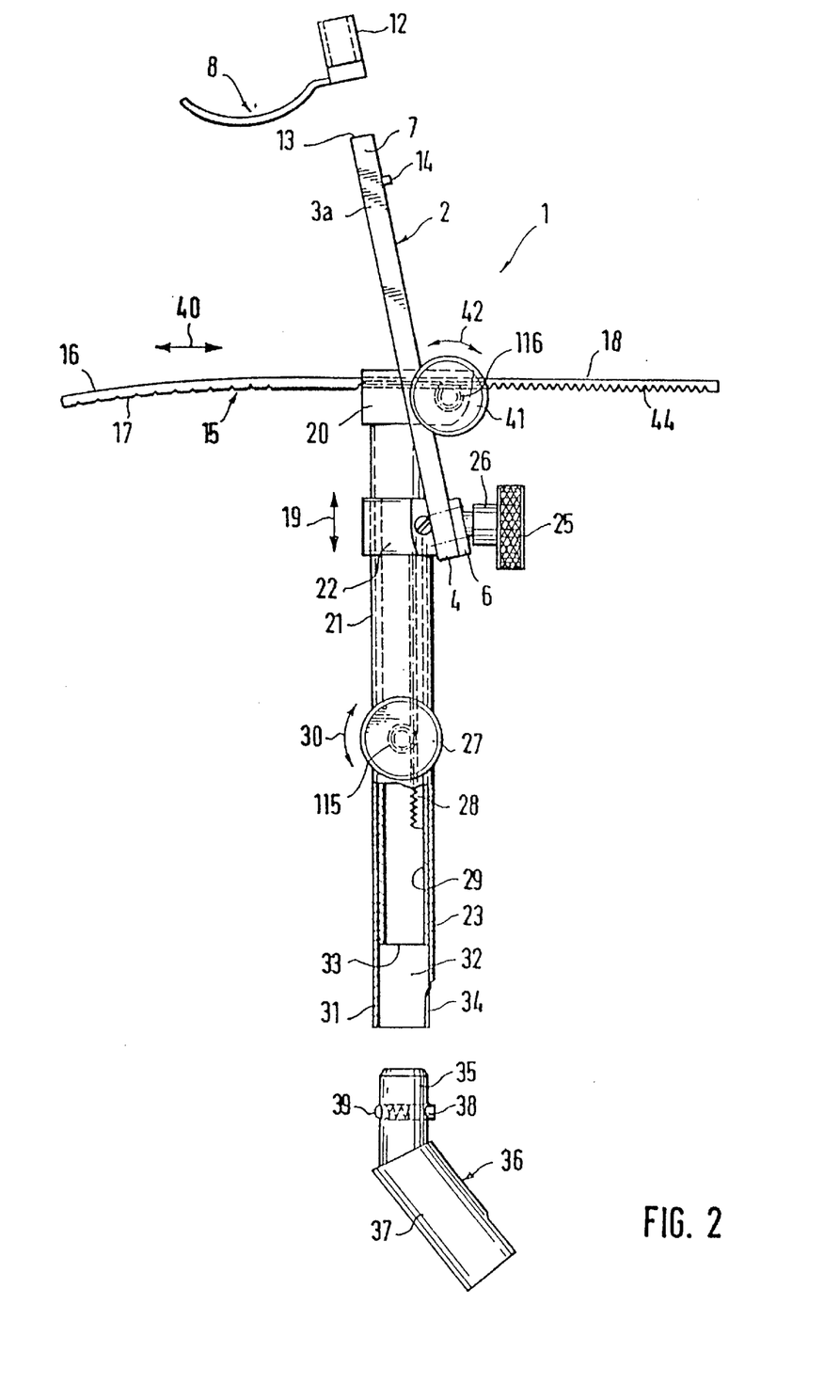
FIG. 2 a side view of FIG. 1 in the direction of arrow II, partly in section.

The palatal plate 8 which has been removed in FIG. 2 but which is shown mounted in FIG. 1 has an approximately circular base surface, which in its longitudinal direction is curved approximately in the form of a saddle, and serves to support the rear region of the hard palate and/or of the processus alveolaris maxillae or of the dentes incisivi.

This palatal plate 8 is stamped, together with a transverse frame-element 9 adjacent to the front edge of said palatal plate, from an approximately 2.5 mm thick sheet of stainless steel and is therefore stable enough to be able to transmit, without causing deformation, the forces that are necessary for locking the maxilla open. In its lateral region the transverse frame-element 9 is spaced, for instance, from the median plane by a distance corresponding to half the width of the palatal plate 8, cranked upwards 10 by an extent amounting to about 1 cm, so that in the distal regions 11 of the transverse frame-element 9 the cavitas oris propria is optimally accessible below the processus alveolaris maxillae and also, in certain circumstances, below the dentes incisivi. At the free ends of the distal regions 11 a sleeve-shaped attachment element 12 is then arranged in each case, in particular it is welded on. These attachment sleeves 12 have a square internal cross-section corresponding approximately to the cross-section of the attachment frame-elements 3a, 3b, and the spacing between the two sleeves 12 that is determined by the proximal part and the two distal parts 11 of the crosspiece 9 corresponds to the spacing between the two upper ends 7 of the two transverse frame-elements 3a, 3b, so that the palatal plate 8 with these sleeves 12 can be attached onto the U-shaped attachment framework. Each of the two attachment frame-elements 3a, 3b comprises, at a spacing of about 1 cm below its upper end face 13, a prolongation 14 projecting approximately horizontally which serves as a stop for the sleeves 12 and prevents the palatal plate 8 from sliding down along the attachment frame-elements 3a, 3b. The longitudinal axes of the two sleeves 12 extend approximately perpendicular to the base surface of the palatal plate 8.

In its capacity as locking device the palatal plate 8 finds its complement in a lingual spatula 15, with which the tongue is pressed against the floor of the mouth and at the same time the mandible is, as a result, locked open in a downward direction. As can be discerned in FIGS. 2 and 3, the lingual spatula 15 has a flat, almost plane shape having approximately the outline of a spoon. The front or tongue part 16 is located with its underside 17 in contact with the tongue of the patient, whereas the rear, stalk-shaped region 18 is retained on the U-shaped attachment framework 2. With a view to attaching the pharyngo-laryngoscope 1 according to the invention, the spacing between the palatal plate 8 and the lingual spatula 15 can firstly be reduced; thereafter the spacing is increased in order to lock the oral cavity open. This displacement movement 19 of the lingual spatula 15 approximately perpendicular to the underside 17 thereof is achieved by the receiving means 20 for the lingual spatula 15 being arranged on a column 21 which is longitudinally displaceable within a sleeve 22. This sleeve 22 is firmly screwed 7 to the crosspiece 6 in such a way that its longitudinal axis and hence also the column 21 extends in the medial plane of the U-shaped attachment framework 2 and also approximately parallel to the two attachment frame-elements 3a, 3b. In reality the base plane of the U-shaped attachment framework 2 is inclined by an angle of about 10° in relation to the longitudinal axis of the column 21 in order at least partly to compensate for the receding of the hard palate in relation to the tongue of the patient during dorsal flexion of the cranium by means of an approximately secant-like orientation of the U-shaped framework 2.

With a view to locking the column 21 in any displacement position in relation to the sleeve-shaped holder 22, on the side 23 of the column 21 facing the crosspiece 6 a longitudinal slot 24 is provided which is penetrated by the shank of a screw 26 that is provided with a knurled head 25, said screw being moreover inserted into a bore in the crosspiece 6 and also in the region of the sleeve-shaped element 22 adjacent thereto. This screw is screwed within an approximately cylindrical clamping element which is located within the column 21 and which in the case where the screw 26 is locked onto the front region 23 of the column 21 is applied thereto in order to bring about fixation of the column by frictional engagement. Prior to the locking of the column 21 in any intermediate position a defined possibility for adjustment 19 is important in order to be able to lock the oral cavity open in gentle yet vigorous manner. A second knurled screw 27 which penetrates a lateral bore in the column 21 is provided for this purpose. However, this screw is provided on its shank not with a thread, as is generally conventional, but with a pinion-type toothed profile 115 which meshes with a toothed rack 28 arranged within the column 21. This toothed rack 28 is connected in non-displaceable manner to the aforementioned cylindrical clamping part which is pressed by the screw 26 for the purpose of locking onto the front 23 inner side 29 of the column 21, so that by displacement of the toothed rack 28 as a consequence of a rotation 30 of the knurled adjusting screw 27 when the locking screw 26 is loosened also the cylindrical clamping part and hence also the guide part 22 is displaced 19 together with the crosspiece 6 in relation to the column 21. It, accordingly, the knurled screw 27 according to FIG. 2 is rotated 30 clockwise, the column 21 travels 19 downwards in relation to the U-shaped framework 2, which is equivalent to raising the palatal plate 8 in relation to the lingual spatula 15 and to locking the oral cavity of the patient open.

Since in this regard the spacing of the mandible in relation to the thorax barely changes, a chest support may be connected to the lower end 31 of the column 21. This column end 31 comprises for this purpose a bushing-like hollow 32 with an inner, peripheral stop shoulder 33 and also an axially parallel notch 34. This receptacle 32 corresponds to the standard peg of commercially available chest supports, the notch 34 serving to insert a clamp screw that is screwed on within the peg of the chest support. Conventional chest supports are in fact usually equipped with an adjustable articulation so that adaptation to the particular application is possible. The capacity for adjustment of such an articulation, however, is often limited, since such supports are optimized for the connection to conventional and hence differently designed laryngoscopes. In order to compensate here for any difference in angle that may arise, the invention provides an angle piece 36 which comprises a peg 35 for the purpose of insertion into the bushing 32, on the one hand, and also a bushing element 37 for the purpose of connection to the chest support, on the other hand. These two parts 35, 37 of the angle piece 36 form an angle of about 140°. A lateral prolongation 38 of the peg 35 engages the notch 34 of the bushing 32 of the pharyngo-laryngoscope 1 according to the invention and thereby avoids twisting of the angle piece 36. Arranged diametrally opposite the prolongation 38 is a spring-mounted ball 39 for producing a frictional engagement between the peg 35 and the bushing 32.

Figure 3:
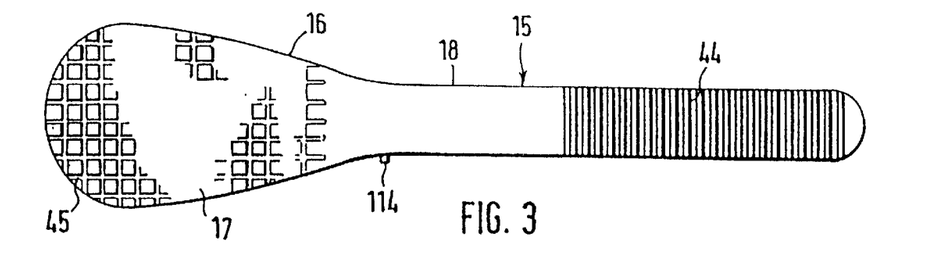
FIG. 3 the underside of the lingual spatula detached from the device according to FIGS. 1 and 2.
Figure 4A:
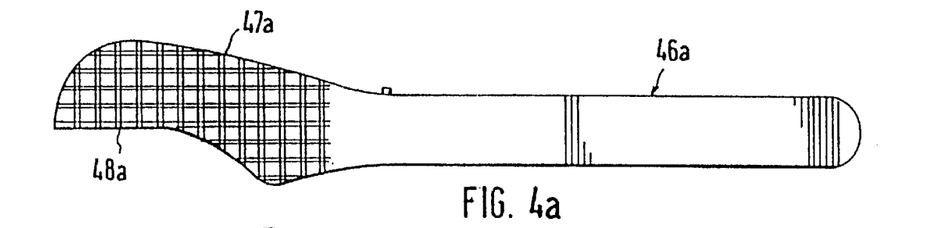
FIGS. 4a, 4b other lingual spatulas with differing shape of the tongue part in a representation corresponding to FIG. 2.
Figure 4B:
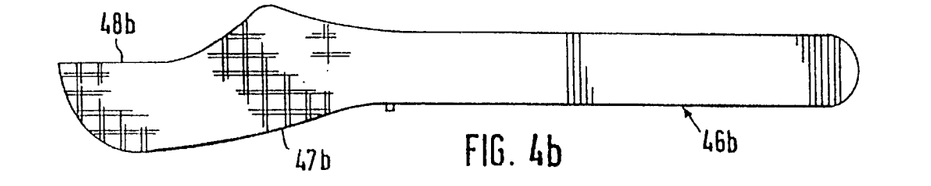

Prior to the oral cavity being locked open it is firstly necessary to adjust the length of the lingual spatula 15 to the patient in question. For this purpose the lingual spatula 15 is displaceably received 40 in the receptacle 20 along its longitudinal axis. To this end the receiving means 20 is constructed as a rail that grips the spatula handle 18 from below, grips round it and grips it at least partly from above, said rail having a constant profile cross-section that is shaped to be approximately complementary to the cross-section of the spatula handle 18. With a view to adjustment 40, a knurled screw 41 is actuated 42, the axis of rotation 43 of which penetrates the receiving part 20 approximately parallel to the rosspiece 6. The shank 43 has, moreover, a length that is greater than one half of the spacing between the two transverse frame-elements 3a, 3b, so that the knurled screw 41 lies outside the oral region of a patient and can be actuated conveniently. The part of the screw means 41 located within the receiving means 20 is profiled in the form of a pinion 116 and meshes with a row of teeth 44 which is produced by milling on the underside 17 of the spatula handle 18. By means of this transmission mechanism the rotary movement 42 of the knurled screw 41 is converted directly into a longitudinal displacement 40 of the lingual spatula 15 which can thereby be optimally adapted to a patient. The lingual spatula 15 is not locked in its longitudinal direction 40, so that when the oral cavity is locked open 19 the spatula 15 can adapt itself to the anatomy of the patient. A stop prolongation 114 avoids jamming of the widened tongue part 16 in the receiving means 20. In order to ensure in this connection that no offset arises between the lingual spatula 15 and the tongue, the underside 17 of the tongue part 16 of the spatula 15 is provided with a grid-type or chequerboard-type profile 45.

Figure 5:
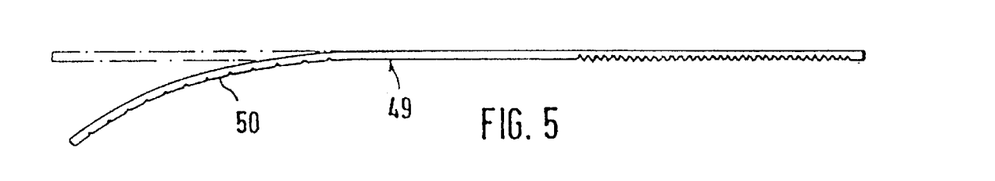
FIG. 5 a lingual spatula that is slightly modified in comparison with FIGS. 3 to 4b, in side view.

Further embodiments of lingual spatulas are represented in FIGS. 4 to 7. Here the spatulas 46a, 46b according to FIGS. 4a, 4b correspond largely to the lingual spatula 15 according to FIG. 3, with the exception that the tongue part 47a, 47b is provided on its right and left sides respectively with a cut-out 48a, 48b in order to expose certain parts of the tongue for diagnostic and/or surgical purposes. In FIG. 5 a further embodiment 49 of a lingual spatula can be seen which may have the basic shape either of the spatula 15 or of a spatula 46a, 46b. Here, however, the tongue part 50 is provided with a longitudinal curvature leading downwards so that the rear region of the tongue is pressed against the hyoid bone in order to create optimal access to the larynx.

Figure 6:
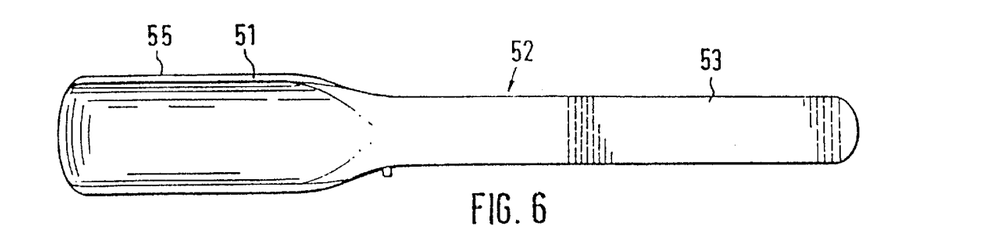
FIG. 6 another lingual spatula according to the invention, in top view.
Figure 7:
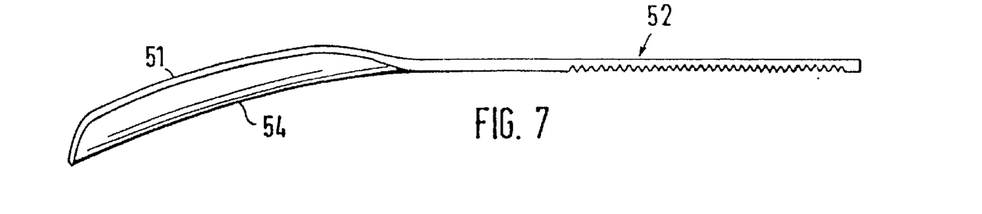
FIG. 7 a side view of the lingual spatula from FIG. 6.

A similar longitudinal curvature is also exhibited by the tongue part 51 of the lingual spatula 52 represented in FIGS. 6 and 7. The latter is formed, as it were, by a combination of the two lingual spatulas 46a, 46b with a relatively narrow tongue part 51 which is barely wider than the handle 53. The underside 54 of the tongue part 51 is furthermore curved in convex manner in the transverse direction in order that the edges 55 of the tongue part 51 do not cut into the tongue.

If the oral cavity is locked open in such a way by means of the palatal plate 8 and a lingual spatula 15, the buccae of the patient can be spread out laterally. Two labial-commissure spatulas 56a, 56b, the left one 56a of which is represented on an enlarged scale in FIG. 8, serve this purpose. It can be discerned that each of the two labial-commissure spatulas consists of a flexible metal sheet having a thickness of about 2 mm and has a length of about 20 to 25 cm. The front region 57 is provided with a rounded edge 58 and also with a profile 59 on the outside 60.

Figure 8:
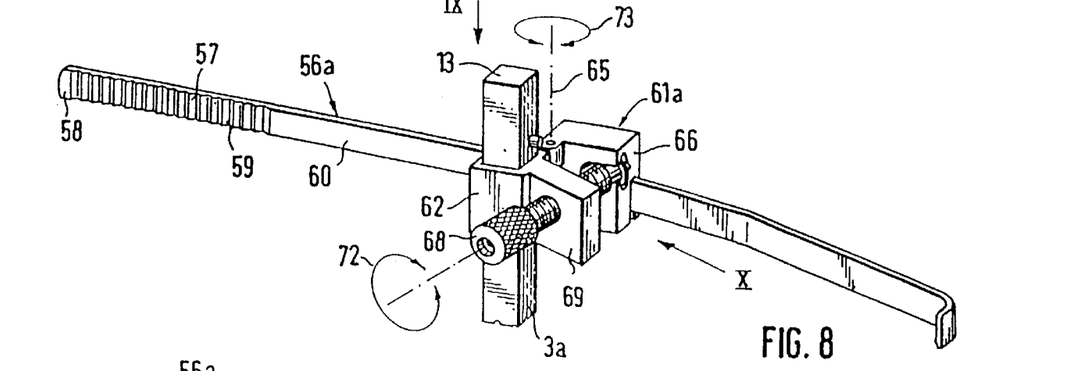
FIG. 8 an axonometric representation of the left labial-commissure spatula from FIG. 1 on an enlarged scale, so that the receiving and spreading means can be identified more clearly.
Figure 9:
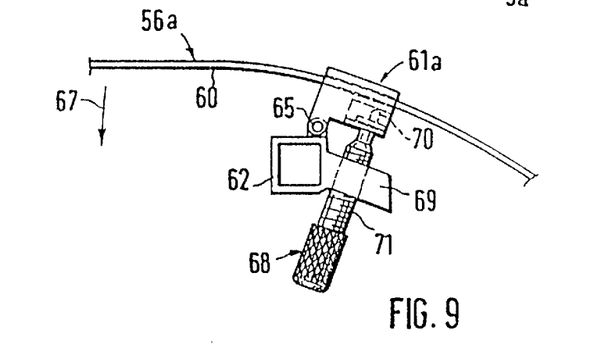
FIG. 9 a top view of FIG. 8 in the direction of arrow IX.
Figure 10:
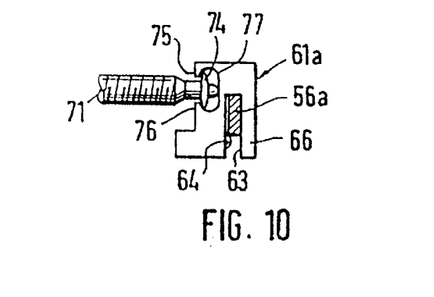
FIG. 10 a side view of the receiving means of FIG. 8 in the direction of arrow X.

For the purpose of fixing and spreading apart these labial-commissure spatulas 56a, 56b, use is made in each case of a receiving means 61a, 61b which is provided with a sleeve 62 of the same geometry as the sleeve 12 of the palatal plate 8. This sleeve 62 is pushed onto each of the two attachment frame-elements 3a, 3b—to be specific below the stop prolongation 14 thereof—so that these receiving means 61a, 61b are held in captive manner on the U-shaped framework 2.

The labial-commissure spatula 56a is inserted into a slot 63 in the receiving means 61a so that the flat, profiled 59 outside 60 of the labial-commissure spatula 56a is oriented parallel to the relevant bucca of the patient, and is fixed in this position by a spring-mounted ball 64. The length of the labial-commissure spatula 56a engaging within the oral cavity can be adjusted by displacement within the slot 63. For the purpose of spreading apart the two labial-commissure spatulas 56a, 56b, use is made of an axis of rotation 65 which is parallel to the longitudinal axis of the attachment frame-element 3a, 3b in question, said axis of rotation connecting the sleeve 62 of the receiving means 61a in articulated manner to the slotted 63 part 66 of the receiving means 61a.

The articulation 65 permits the front region 57 of the labial-commissure spatula 56a in question to be spread apart 67; for the purpose of exact adjustment of the spreading angle 67, use is made of an additional knurled screw 68 which is screwed into a threaded bore in a rear, flap-type prolongation 69 of the sleeve 62. The front end face 70 of the screw shank 71 presses against the slotted part 66 so that the rotary adjustment 72 of the knurled screw 68 is converted into a swivelling movement 73 of the slotted receiving part 66 about the axis of rotation 65 and finally results in the labial-commissure spatula 56a in question being spread apart 67.

In order with the aid of knurled screw 68 also to be able to cause the two labial-commissure spatulas 56a, 56b to swivel together, in the region of the front end face 70 of the screw shank 71 a circular disk 74 is molded on which is partly gripped from the rear by two undercuts 75, 76 of the slotted part 66 which are parallel to one another. Between the two undercuts 75, 76 a slot remains for passage of the screw shank 71. Depending on the rotary movement 72 of the knurled screw 68, therefore either the front end face 70 thereof presses against the bottom 77 of the undercut region (spreading-apart 67) or the circular disk 74 pulls the slotted part 66 against the flap-type prolongation 69 via the undercuts 75, 76, whereby the front region 57 of the labial-commissure spatula 56a is swivelled towards the median plane of the patient.

After the oral cavity has been locked open and the buccae of a patient have been spread apart in such a way, it is possible to provide for illumination of the pharynx. To this end the physician makes use of a lighting means 78 that has been specially designed to be appended to the attachment framework 2 according to the invention and is represented in FIG. 1. Said lighting means consists of a cylindrical socket 79, into which a system of lenses is pressed. Screwed on a rear thread prolongation of the socket 79 is an adapter 80 which has approximately the shape of a cylindrical sheath and is provided on its rear end face 81 with a special connecting thread 82 for screwing on a connecting element of a fibre-optic cable which is not represented in FIG. 1. Arranged on the socket part 79 is an attachment block 83 which acquires its approximately U-shaped form by virtue of a slot 84. The slot 84 has approximately the cross-section of an attachment frame-element 3a, 3b, so that the lighting means 78 can optionally be firmly clamped to both frame-elements 3a, 3b. For the purpose of locking, use is made of a spring-mounted ball which cannot be discerned in FIG. 1, 25 said ball being similar to the ball 39 of the angle part 36 or the ball 64 of the receiving means 61a. Furthermore, a ball-and-socket joint 85 is provided between the socket 79 and the attachment block 83, in order that the luminous cone of the lighting means 78 can be adjusted exactly.

An examination or operation can now be undertaken in the region of the pharynx or of the larynx. In the course of an operation, a tumor-grasping forceps 86 is often required, such as is also represented in FIG. 1. Said grasping forceps consists of a hollow tube 87 in which a rod 88 is inserted in telescopic manner which at its front end is subdivided in the axial direction and is also spread apart radially so as to form several pincer-like gripping elements 89. Arranged between the rear ends of the telescopic tube 87 and also of the telescopic rod 88 is a leaf spring 90 bent in the form of a U which, on the one hand, closes the grasping elements 89 of the forceps 86 automatically and, on the other hand, serves as a handle.

Figures 11, 12, 13:
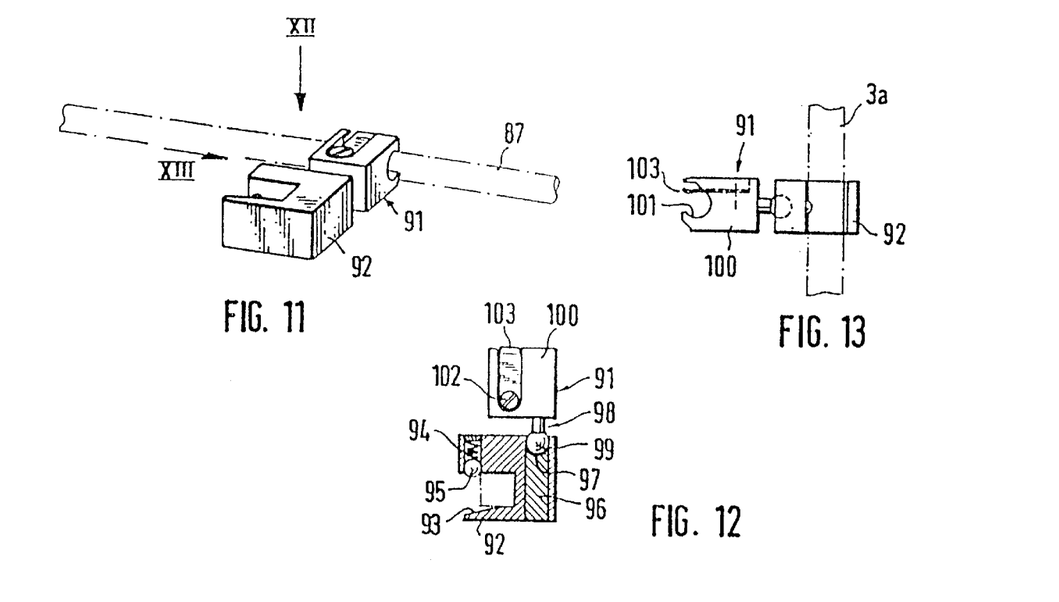
FIG. 11 another receiving means for securing an instrument to the device according to the invention, in an axonometric representation.
FIG. 12 a top view of FIG. 11 in the direction of arrow XII, partly in section.
FIG. 13 a side view of the receiving means from FIG. 11 in the direction of arrow XIII.

In order to be able to work accurately with such a grasping forceps 86, the latter is also secured to a point on the attachment framework 2. To this end use is made of an additional standard receiving means 91 represented in FIGS. 11 to 13. Said standard receiving means consists of an attachment block 92 for securing to one of the two attachment frame-elements 3a, 3b, which is identical with the attachment block 83 of the lighting means 78. In particular in FIG. 12 it is possible to discern the slot 93 for the purpose of firm clamping to an attachment frame-element 3a, 3b and also the spring-mounted 94 ball 95 for the purpose of locking by frictional engagement. Finally, molded in the yoke region 96 of the cross-sectionally U-shaped attachment block 92 is the socket 97 of a ball-and-socket joint 98, the ball 99 of which is connected to the actual receiving block 100. As can be gathered from FIG. 13, the receiving block 100 is provided on its side located opposite the ball 99 with a slot 101 for insertion of the telescopic tube 87 of the tumor-grasping forceps 86. A leaf spring 103 firmly screwed 102 to the receiving block 100 springs radially into the receiving slot 101 and thereby secures the telescopic tube 87 within the slot 101. The tumor-grasping forceps 86 is thereby self-locking in every position and yet can be displaced in the longitudinal direction within the slot 101 and can in addition be swivelled about the ball-and-socket joint 98.

In a manner similar to that in the case of the tumor-grasping forceps 86, a plurality of additional examining and/or surgical instruments may also be inserted in a standard receiving means 91, in particular also an instrument for laser surgery or laser coagulation of course, with such surgical laser interventions an intense generation of smoke occurs which hinders the view and which could thereby nullify many of the advantages of the pharyngo-laryngoscope 1 according to the invention. Therefore the invention further provides a smoke-suction device 104 as represented in FIG. 1. Said smoke-suction device comprises a tubular piece 105 that projects into the oral cavity, on the front end of which is pushed a gently curved sleeve 107 provided with perforations 106 with a view to avoiding injuries. The tube 105 is stiffened by means of an inserted and/or infused metallic wire and is attached by its rear end onto an elbow 108 which is provided at its rear end 109 with a tube-connecting piece 110 for the purpose of pushing on a rubber tube that is connected to a suction device. This connecting piece 110 tapers in approximately conical manner towards its free end in order to enable rubber tubes of variable cross-section to be pushed on. Furthermore, this connecting piece 110 is provided on its outside with peripheral beads in order to prevent a rubber tube that has been pushed on from sliding down.

For the purpose of clamping such a suction device 104 firmly, use is made of a receiving means 111 which comprises, in a manner similar to the standard receiving means 91, an attachment block 112 for the purpose of clamping on one of the two attachment frame-elements 3a, 3b, on which, however, a slotted receiving block 113 is rigidly molded—ie, without a ball-and-socket joint.

What is claimed is:

1. A device (1) for endoscopic examinations and operations, comprising a framework (2) and at least one of holding means (32), connecting means (12; 83) and receiving means (20; 61a, 61b; 91; 111), for locking elements, spreading elements (8), lingual spatulas (15; 46a, 46b; 49; 52), labial-commissure spatulas (56a, 56b), lighting means (78), suction devices (104) for, fluids including smoke, examining instruments, including endoscopes, surgical instruments, including grasping forceps (86) and laser instruments for laser surgery and laser coagulation, wherein said holding means (32), connecting means (12; 83) and receiving means (20; 61a, 61b; 91; 111 ) are arranged on the framework (2); and a toothed rack (28) with which the position of a column (21) bearing the receiving means (20) for the lingual spatula (15) is manually adjustable in relation to a guide element (22) of the attachment framework (2).

2. The device as claimed in claim 1, wherein two stable frame-elements (3a, 3b) approximately parallel to one another are present on the attachment framework (2) for the purpose of securing displaceable connecting means (12; 83), receiving means (61a, 61b; 91; 111), for labial-commissure spatulas (56a, 56b), lighting means (78), suction devices (104), examining instruments and surgical instruments (86).

3. The device as claimed in claim 2, wherein the attachment frame-elements (3a, 3b) have a square cross-section.

4. The device as claimed in claim 2, wherein the two attachment frame-elements (3a, 3b) are connected to one another by means of a crosspiece so as to form a substantially U-shaped attachment framework (2).

5. The device as claimed in claim 4, wherein the attachment frame-elements (3a, 3b) are displaceable in relation to the crosspiece (6) about axes of rotation that extend perpendicular to the base surface of the U-shaped attachment framework (2).

6. The device as claimed in claim 4, wherein at least one of said receiving means (20; for one of a lingual spatula (15) and a chest support, and are arranged on the crosspiece (6) of the attachment framework (2).

7. The device as claimed in claim 6, wherein the receiving means (20) is for the lingual spatula (15) and is arranged such that a longitudinal axis of the lingual spatula (15) extends substantially perpendicular to a base plane of the U-shaped attachment framework (2).

8. The device as claimed in claim 7, wherein the receiving means (20) for the lingual spatula (15) is displaceable in relation to the crosspiece (6) along an axis (21) which is substantially perpendicular to the attachment frame-elements (3a, 3b).

9. The device as claimed in claim 8, wherein the receiving means (20) for the lingual spatula (15) is arranged at one end of a column (21) which is guided displaceably (19) in a tube-shaped guide element (22) of the crosspiece (6).

10. The device as claimed in claim 9, wherein the guide element (22) for the column (21) bearing the lingual spatula (15) is arranged in a substantially centric manner on the crosspiece (6) of the U-shaped attachment framework (2) so that the attachment framework (2) together with the column (21) forms shape of one of a Y and a trident.

11. The device as claimed in claim 9, comprising a device (25, 26) for locking the column (21) bearing the receiving means (20) for the lingual spatula (15) in relation to the guide element (22) of the attachment framework (2).

12. The device as claimed in claim 6, wherein the receiving means (20) for the lingual spatula (15) permits a displacement (40) of the spatula in its longitudinal direction.

13. The device as claimed in claim 12, wherein the receiving means (20) for the lingual spatula (15) comprises a guide profile surrounding the handle (18) of said lingual spatula at least partly.

14. The device as claimed claim 6, wherein the connecting means for a chest support is connected to the crosspiece (6) of the attachment framework (2) via a prolongation which extends substantially perpendicular to the longitudinal axis of the lingual spatula (15).

15. The device as claimed in claim 14, wherein the connecting means for the chest support is arranged on an end face of the longitudinally displaceable column (21) located opposite the receiving means (20) for the lingual spatula (15).

16. The device as claimed in claim 14, wherein the connecting means for the chest support comprises a hollow cylindrical bushing (32).

17. A device (1) for endoscopic examinations and operations, said device comprising a framework (2) and at least one of holding means (32), connecting means (12; 83) and receiving means (20; 61a, 61b; 91; 111), for locking elements, spreading elements, lingual spatulas (15; 46a, 46b, 49; 52), labial-commissure spatulas (56a, 56b), lighting means (78), suction devices (104) for fluids, including smoke, examining instruments, including endoscopes, surgical instruments, including grasping forceps (86) and laser instruments for laser surgery and laser coagulation, wherein said holding means (32), connecting means (12; 83) and receiving means (20; 61a, 61b; 91; 111) are arranged on the framework (2), and a screw mechanism (41), for at least one of adjustment and locking of a displacement position (40) of the lingual spatula (15) in relation to the receiving device (20).

18. A device (1) for endoscopic examinations and operations, said device comprising a framework (2) and at least one of holding means (32), connecting means (12; 83) and receiving means (20; 61a, 61b; 91; 111), for locking elements, spreading elements, lingual spatulas (15; 46a, 46b, 49; 52), labial-commissure spatulas (56a, 56b), lighting means (78), suction devices (104) for fluids, including smoke, examining instruments, including endoscopes, surgical instruments, including grasping forceps (86) and laser instruments for laser surgery and laser coagulation, wherein said holding means (32), connecting means (12; 83) and receiving means (20; 61a, 61b; 91; 111) are arranged on the framework (2), and an angle piece (36) for bringing about an angle between a chest support and a framework-side connection bushing (32) of said device (1), said angle piece comprising a peg (35) for insertion into the connecting bushing (32) of the framework (2), said peg being connected to a bushing (37) for insertion of the connecting peg of the chest support at an obtuse angle.

19. A device (1) for endoscopic examinations and operations, said device comprising a framework (2) and at least one of holding means (32), connecting means (12; 83) and receiving means (20; 61a, 61b; 91; 111), for locking elements, spreading elements, lingual spatulas (15; 46a, 46b, 49; 52), labial-commissure spatulas (56a, 56b), lighting means (78), suction devices (104) for fluids, including smoke, examining instruments, including endoscopes, surgical instruments, including grasping forceps (86) and laser instruments for laser surgery and laser coagulation, wherein said holding means (32), connecting means (12; 83) and receiving means (20; 61a, 61b; 91; 111) are arranged on the framework (2), a lingual spatula (15; 46a, 46b; 49; 52) for insertion into the receiving means (20) said spatula comprising a substantially spoon-type tongue part (16; 47a, 47b; 51) and a straight holding part (18; 53) adjacent thereto which is one of not inclined and only slightly inclined in relation to the tongue part (16; 47a, 47b; 51), the entire lingual spatula (16; 46a, 46b; 49; 52) being produced from a rigid and solid material, wherein the holding part (18; 53) comprises several teeth (44) arranged in a row along its longitudinal axis which mesh with a toothed wheel of a framework-side transmission mechanism (41, 43) with a view to longitudinal displacement (40) of the lingual spatula (15; 46a, 46b; 49; 52).

20. The lingual spatula (46a, 46b) as claimed in claim 19, wherein the tongue part (47a, 47b) is provided with a lateral cut-out (48a, 48b) to enable examinations and operations in a lingual region.

21. The lingual spatula (52) as claimed in claim 19, wherein the tongue part (51) is provided with a curvature in a transverse direction in such a way that lateral regions (55) of the tongue part (51) diverge upwards from a tongue.

22. A device (1) for endoscopic examinations and operations, said device comprising a framework (2) and at least one of holding means (32), connecting means (12; 83) and receiving means (20; 61a, 61b; 91; 111), for locking elements, spreading elements, lingual spatulas (15; 46a, 46b, 49; 52), labial-commissure spatulas (56a, 56b), lighting means (78), suction devices (104) for fluids, including smoke, examining instruments, including endoscopes, surgical instruments, including grasping forceps (86) and laser instruments for laser surgery and laser coagulation, wherein said holding means (32), connecting means (12; 83) and receiving means (20; 61a, 61b; 91; 111) are arranged on the framework (2), and a toothed rack (28) with which the position of a column (21) bearing the receiving means (20) for the lingual spatula (15) is manually adjustable in relation to a guide element (22) of the attachment framework (2), a palatal plate (8) comprising a frame-element (9) with bushings arranged at its end for attaching onto free ends (13) of the attachment framework.

23. The device as claimed in claim 22, wherein the frame-element (9) is adapted to be cranked (10) downwards on both sides with a view to receiving molar teeth and upper jaw of a patient.

24. A device (1) for endoscopic examinations and operations, said device comprising a framework (2) and at least one of holding means (32), connecting means (12; 83) and receiving means (20; 61a, 61b; 91; 111), for locking elements, spreading elements, lingual spatulas (15; 46a, 46b, 49; 52), labial-commissure spatulas (56a, 56b), lighting means (78), suction devices (104) for fluids, including smoke, examining instruments, including endoscopes, surgical instruments, including grasping forceps (86) and laser instruments for laser surgery and laser coagulation, wherein said holding means (32), connecting means (12; 83) and receiving means (20; 61a, 61b; 91; 111) are arranged on the framework (2), and a labial-commissure spatula (56a, 56b) for use as part of said device (1) and comprising an elongated, narrow basic shape with a rounded front edge (58), a means (61a; 61b) for receiving the labial-commissure spatula (56a; 56b) and for securing the same to the attachment framework (2) of said device (1), said means comprising a sleeve-shaped element (62) which encompasses an attachment frame-element (3a; 3b) of the attachment framework (2), a clip-like element (66) with a slot (63) for insertion of the labial-commissure spatula (56a; 56b), and an adjusting means (68) arranged between said sleeve-shaped element (62) and said clip-like element (66) with a view to spreading the labial-commissure spatula (56a, 56b) apart.

25. The labial-commissure spatula as claimed in claim 24 and produced from a flexible material.

26. A device (1) for endoscopic examinations and operations, said device comprising a framework (2) and at least one of holding means (32), connecting means (12; 83) and receiving means (20; 61a, 61b; 91; 111), for locking elements, spreading elements, lingual spatulas (15; 46a, 46b, 49; 52), labial-commissure spatulas (56a, 56b), lighting means (78), suction devices (104) for fluids, including smoke, examining instruments, including endoscopes, surgical instruments, including grasping forceps (86) and laser instruments for laser surgery and laser coagulation, wherein said holding means (32), connecting means (12; 83) and receiving means (20; 61a, 61b; 91; 111) are arranged on the framework (2), wherein two stable frame-elements (3a, 3b) are substantially parallel to one another and are present on the attachment framework (2) for the purpose of securing displaceable connecting means (12; 83) and receiving means (61a, 61b; 91; 111), for labial-commissure spatulas (56a, 56b), lighting means (78), suction devices (104), examining instruments and/or surgical instruments (86), and means (91; 111) for receiving a suction device (104), an examining instrument and a surgical instrument (86), and for securing the same to the framework (2), said means for receiving comprising a clip-type element (100; 113) with a slot (101) for insertion of the device (104) and of the instrument (86), and a clip (92; 112) for securing to said attachment frame-element (3a; 3b) of the attachment framework (2).

27. The lighting means (78) as claimed in claim 26, wherein the attachment clip (83) is provided with a springing element (94).

28. The receiving means (91) as claimed in claim 26, wherein a ball and socket joint (98) is arranged between the attachment clip (92) and the slotted (101) clip element (100).

29. The receiving means (91; 111) as claimed in claim 26, wherein the slotted clip type element (100; 113) is provided with a springing element (95; 103).

30. A device (1) for endoscopic examinations and operations, said device comprising a framework (2) and at least one of holding means (32), connecting means (12; 83) and receiving means (20; 61a, 61b; 91; 111), for locking elements, spreading elements, lingual spatulas (15; 46a, 46b, 49; 52), labial-commissure spatulas (56a, 56b), lighting means (78), suction devices (104) for fluids, including smoke, examining instruments, including endoscopes, surgical instruments, including grasping forceps (86) and laser instruments for laser surgery and laser coagulation, wherein said holding means (32), connecting means (12; 83) and receiving means (20; 61a, 61b; 91; 111 ) are arranged on the framework (2), wherein two stable frame-elements (3a, 3b) are substantially parallel to one another and are present on the attachment framework (2) for the purpose of securing displaceable connecting means (12; 83) and receiving means (61a, 61b; 91; 111), for labial-commissure spatulas (56a, 56b) lighting means (78), suction devices (104), examining instruments and surgical instruments (86), and a lighting means (78) for use as part of said device (1) and comprising a clip (83) for securing to an attachment frame-element (3a; 3b) of the attachment framework (2), and wherein a ball and socket joint (98) is arranged between the attachment clip (83) and the lighting means (78).

* * * * *